(12) United States Patent
Samproni et al.

(10) Patent No.: US 10,746,724 B2
(45) Date of Patent: Aug. 18, 2020

(54) SENSOR ARRAY

(71) Applicant: Siemens Healthcare Diagnostics Inc., Tarrytown, NY (US)

(72) Inventors: Jennifer A. Samproni, Braintree, MA (US); Todd Andrade, New Bedford, MA (US); Marlene Shi, Foxboro, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 209 days.

(21) Appl. No.: 15/748,321

(22) PCT Filed: Jul. 25, 2016

(86) PCT No.: PCT/US2016/043874
§ 371 (c)(1),
(2) Date: Jan. 29, 2018

(87) PCT Pub. No.: WO2017/019609
PCT Pub. Date: Feb. 2, 2017

(65) Prior Publication Data
US 2018/0217127 A1    Aug. 2, 2018

Related U.S. Application Data

(60) Provisional application No. 62/198,882, filed on Jul. 30, 2015.

(51) Int. Cl.
*G01N 33/49* (2006.01)
*G01N 15/00* (2006.01)

(52) U.S. Cl.
CPC ....... *G01N 33/4915* (2013.01); *G01N 33/492* (2013.01); *G01N 2015/0065* (2013.01)

(58) Field of Classification Search
CPC ............ G01N 33/4915; G01N 33/492; G01N 2015/0065
See application file for complete search history.

(56) References Cited

U.S. PATENT DOCUMENTS

| | | | |
|---|---|---|---|
| 2008/0248457 A1* | 10/2008 | Hosoya | G01N 27/26 435/4 |
| 2011/0272295 A1* | 11/2011 | Lee | G01N 27/3272 205/792 |
| 2014/0054170 A1* | 2/2014 | Tsukahara | G01N 27/327 204/403.01 |
| 2015/0082874 A1 | 3/2015 | Samproni et al. | |

FOREIGN PATENT DOCUMENTS

| | | |
|---|---|---|
| WO | 9743634 A1 | 11/1997 |
| WO | 2016011308 A1 | 1/2016 |

OTHER PUBLICATIONS

International Search Report and Written Opinion of International Application No. PCT/US2016/043874 dated Oct. 6, 2016.
European Search Report and Written Opinion of European Application No. 16831194.2 dated Jul. 16, 2018.

* cited by examiner

*Primary Examiner* — Dennis White
(74) *Attorney, Agent, or Firm* — Dunlap Codding P.C.

(57) ABSTRACT

In the various illustrative embodiments herein, test devices are described with opposing sensor arrays and same side contacts.

7 Claims, 4 Drawing Sheets

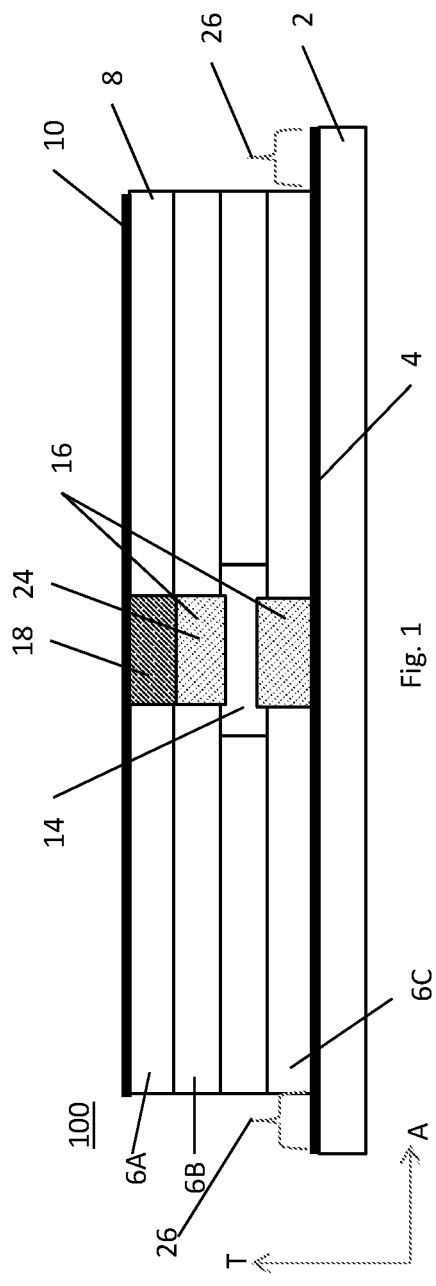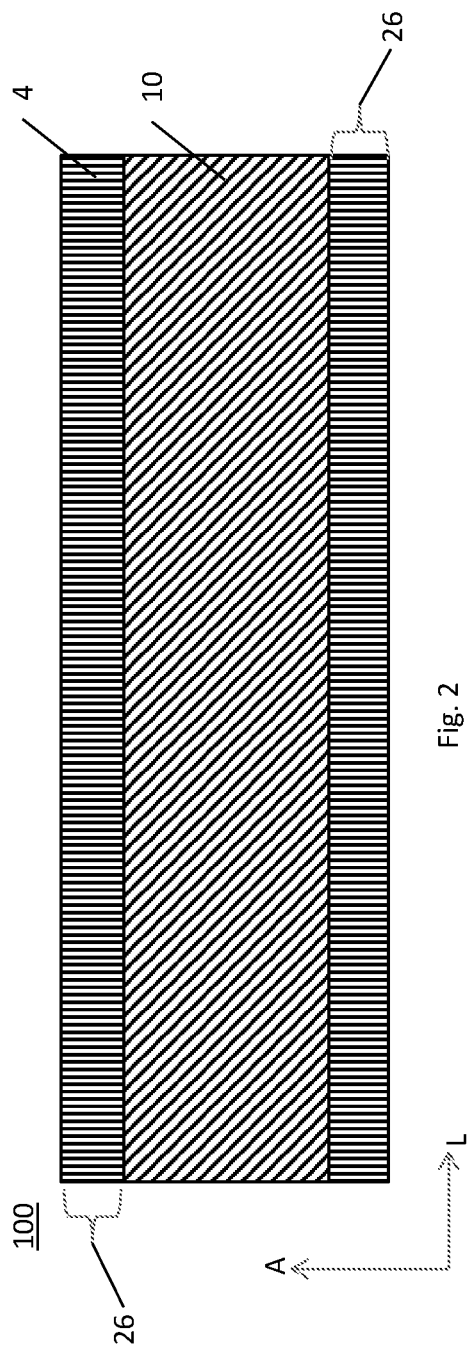

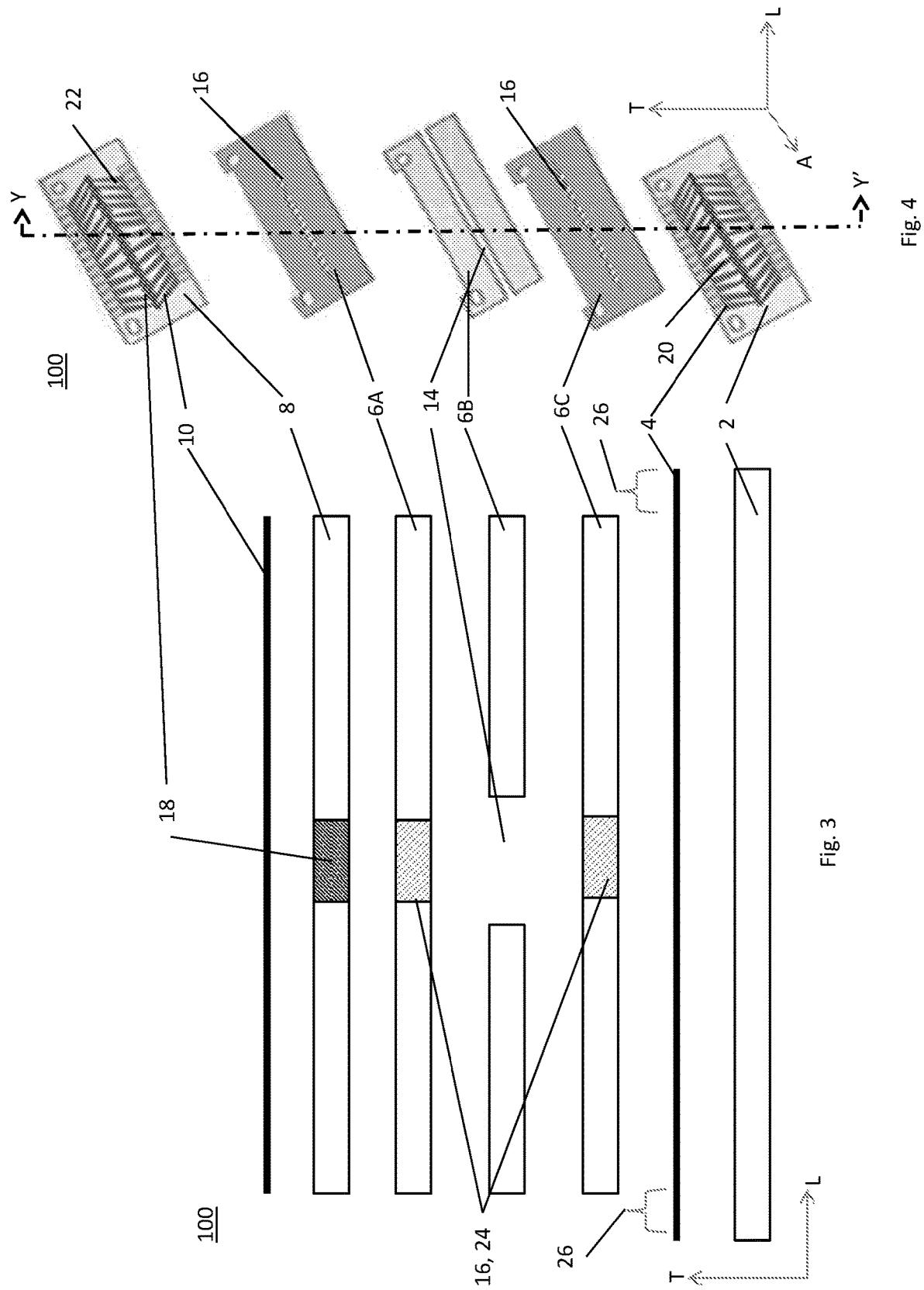

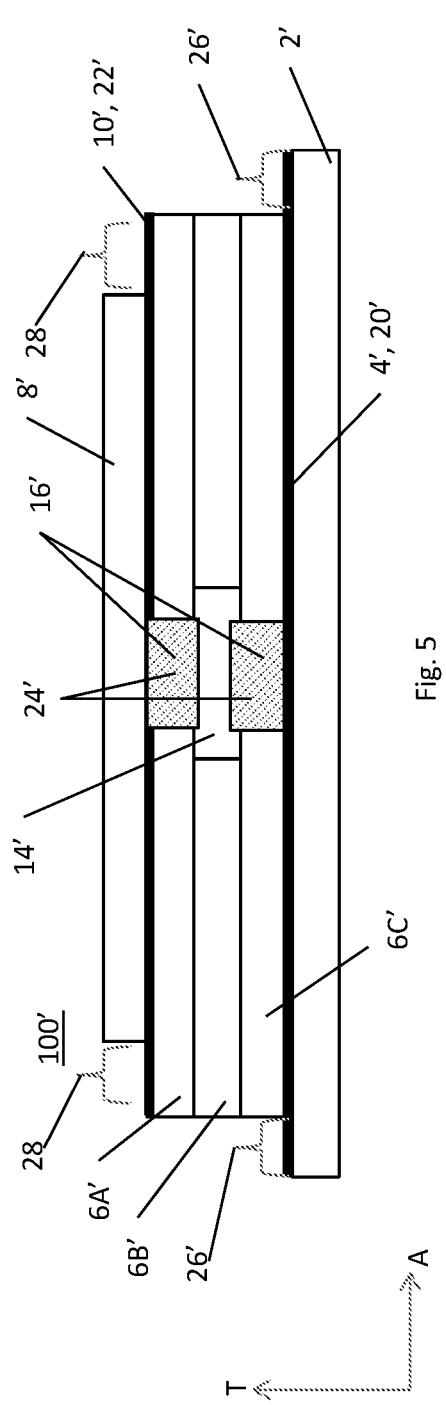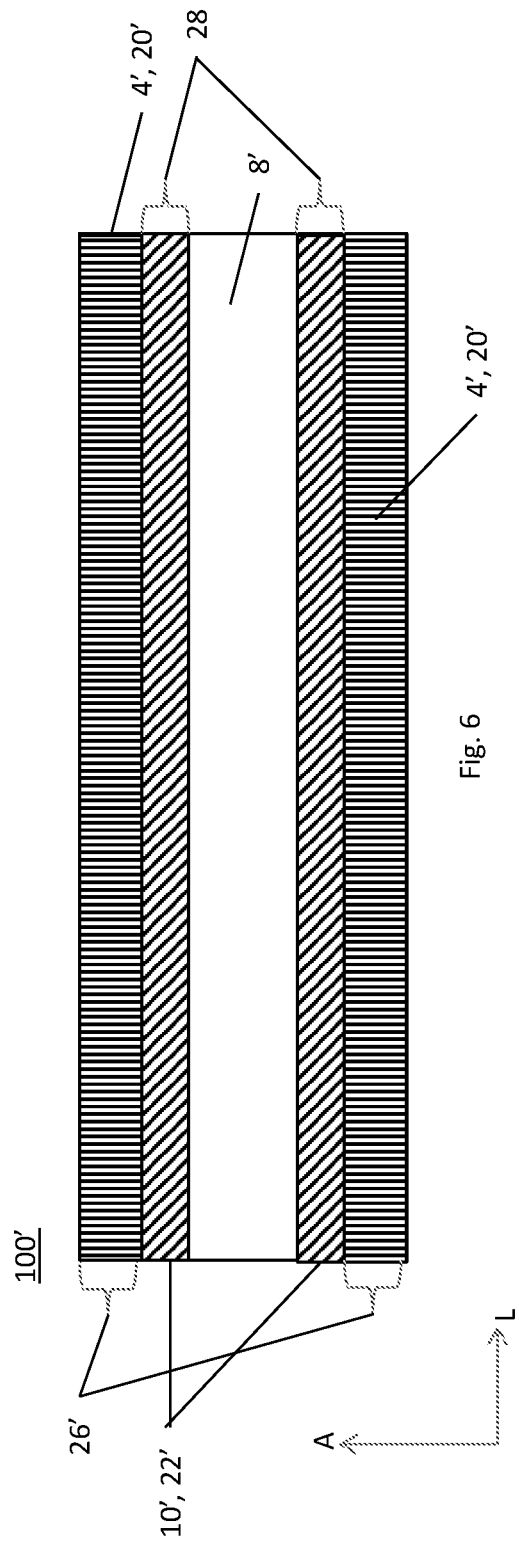

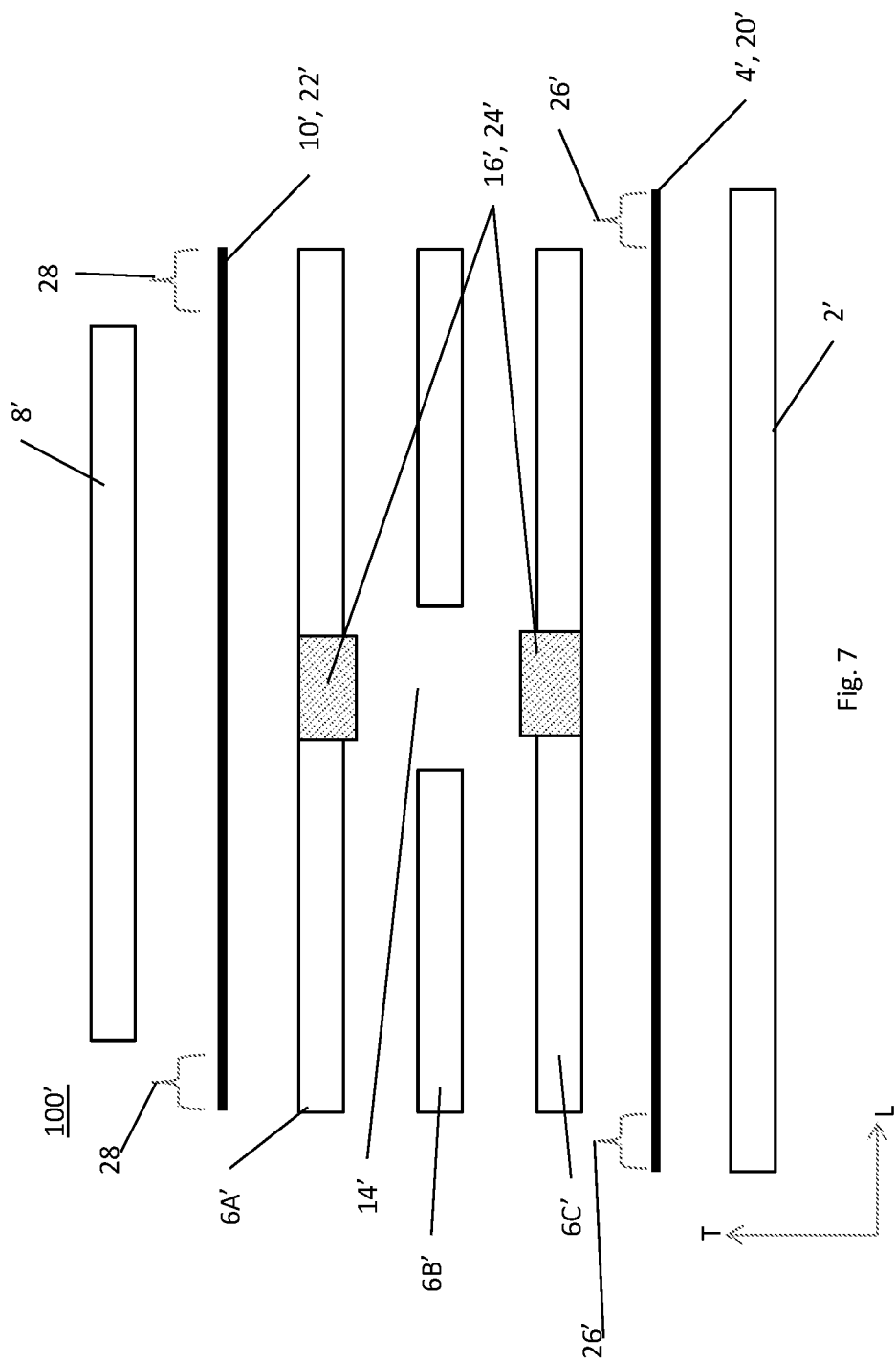

SENSOR ARRAY

The subject application claims benefit under 35 USC § 119(e) of U.S. Provisional Application No. 62/198,882, filed Jul. 30, 2015. The entire content of the above-referenced patent application is hereby expressly incorporated herein by reference.

BACKGROUND

This disclosure relates to a sensing device which allows for multiple tests to be run concurrently using a small sample volume.

SUMMARY OF THE INVENTIVE CONCEPT(S)

In the various illustrative embodiments herein, test devices are described with opposing sensor arrays and same side contacts.

BRIEF DESCRIPTIONS OF THE DRAWINGS

FIG. 1 depicts side view of a first embodiment of the low-volume sensing device.

FIG. 2 depicts a top view of the first embodiment of the low-volume sensing device.

FIG. 3 depicts an exploded side view of the first embodiment of the low-volume sensing device.

FIG. 4 depicts an exploded perspective view of the first embodiment of the low-volume sensing device.

FIG. 5 depicts a side view of a second embodiment of the low-volume sensing device.

FIG. 6 depicts a top view of the second embodiment of the low-volume sensing device.

FIG. 7 depicts an exploded side view of the second embodiment of the low-volume sensing device.

DETAILED DESCRIPTION OF THE INVENTIVE CONCEPT(S)

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. The inventive concepts disclosed herein are capable of other embodiments or of being practiced or carried out in various ways. Also, it is to be understood that the phraseology and terminology employed herein is for the purpose of description and should not be regarded as limiting the inventive concepts disclosed and claimed herein in any way.

In the following detailed description of embodiments of the inventive concepts, numerous specific details are set forth in order to provide a more thorough understanding of the inventive concepts. However, it will be apparent to one of ordinary skill in the art that the inventive concepts within the instant disclosure may be practiced without these specific details. In other instances, well-known features have not been described in detail to avoid unnecessarily complicating the instant disclosure.

As used herein, the terms "comprises," "comprising," "includes," "including," "has," "having" or any other variation thereof, are intended to cover a non-exclusive inclusion. For example, a composition, a process, method, article, or apparatus that comprises a list of elements is not necessarily limited to only those elements but may include other elements not expressly listed or inherently present therein.

As used herein the terms "approximately," "about," "substantially" and variations thereof are intended to include not only the exact value qualified by the term, but to also include some slight deviations therefrom, such as deviations caused by measuring error, manufacturing tolerances, wear and tear on components or structures, settling or precipitation of cells or particles out of suspension or solution, chemical or biological degradation of solutions over time, stress exerted on structures, and combinations thereof, for example.

As used herein, the term "sample" and variations thereof is intended to include biological tissues, biological fluids, chemical fluids, chemical substances, suspensions, solutions, slurries, mixtures, agglomerations, tinctures, slides, powders, or other preparations of biological tissues or fluids, synthetic analogs to biological tissues or fluids, bacterial cells (prokaryotic or eukaryotic), viruses, single-celled organisms, lysed biological cells, fixed biological cells, fixed biological tissues, cell cultures, tissue cultures, genetically engineered cells and tissues, genetically engineered organisms, and combinations thereof, for example.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present). An inclusive or may be understood as being the equivalent to: at least one of condition A or B.

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Finally, the embodiments of the low-volume sensing device disclosed herein may be understood with reference to a first, second, and third direction such as, for example, lateral direction 'A', a longitudinal direction 'L' which is perpendicular to lateral direction 'A', and a transverse direction 'T' which is perpendicular to longitudinal direction 'L.' The longitudinal direction L and the lateral direction A extend horizontally as illustrated, and the transverse direction T extends vertically, though it should be appreciated that these directions may change depending, for instance, on the orientation of the low-volume sensing device. It should also be understood that first direction may be referred to as the lateral direction. It should also be understood that second direction may be referred to as the longitudinal direction. It should also be understood that third direction may be referred to as the transverse direction.

The inventive concepts disclosed herein are generally directed to the need to minimize the sample volume required to test two or more analytes concurrently. Low sample volumes are desirable when the sample is limited, such as in the case of whole blood from neonatal patients, or when the sample itself is expensive. As opposed to prior art test devices configurations, which required the volume to increase with the number of analytes being detected, the required sample volume can be greatly reduced when the two planar arrays of sensors are arranged in such a way that they are facing one another in a sandwich configuration (also referred to as an opposing sensor array) as opposed to a configuration in which each sensor is arranged in a coplanar configuration. Furthermore, in order to simplify the manner in which test devices with opposing sensor arrays interface with medical instruments, the testing device can be configured such that its electrical contacts can be easily accessed. This configuration maximizes the number of sensors that can be incorporated into a single test device while simplifying the manner in which the device interfaces with the medical instrument. It should be understood that the term "test device," and variations thereof, include single use or multi use devices as well as disposable "test strips."

In accordance with the inventive concepts described herein, illustrative embodiments of low-volume sensing devices with opposing sensor arrays are discussed in connection with FIGS. 1 through 7 below.

FIGS. 1-4 depict a first embodiment a low-volume sensing device. FIG. 1 depicts a side view of a first embodiment of the low-volume sensing device along line Y-Y' from FIG. 4. FIG. 2 depicts a top view of the first embodiment of the low-volume sensing device. FIG. 3 depicts an exploded side view of the first embodiment of the low-volume sensing device along line Y-Y' from FIG. 4. FIG. 4 depicts an exploded perspective view of the first embodiment of the low-volume sensing device.

Test device 100 contains a first planar substrate 2. Planar substrate 2 may be substantially planar with a substantially planar upper surface and substantially planar lower surface of the planar substrate 2—both of which extend in the lateral direction A and the longitudinal direction L (as shown in FIG. 2) and are separated by a thickness extending along the transverse direction T.

Test device 100 further includes planar conductive layer 4 disposed on or adjacent to the upper surface of planar substrate 2. Stated differently, conductive layer 4 is disposed above planar substrate 2 along the transverse direction T and is coplanar with the upper surface of planar substrate 2. While conductive layer 4 includes one or more individual coplanar electrodes 20, as shown in FIG. 4, conductive layer 4 is represented by the designated shaded area in FIG. 2. Coplanar electrodes 20 may be formed using a variety of methods and materials known to a person of ordinary skill in the art. For example, coplanar electrodes 20 may be formed using a thick film approach (e.g., screen printing, rotogravure, pad printing, stenciling, ink jetting or aerosol jetting conductive material such as carbon, Cu, Pt, Pd, Au, and/or Nanotubes (such as carbon nanotubes), etc. . . . ) or a thin film approach (e.g., by sputtering, thermal spraying, and/or cold spraying conductive material). Coplanar electrodes 20 may be partitioned using, for example, laser ablation. It should be understood that the configuration of electrodes 20 depicted herein are merely for illustrative purposes only and a person of ordinary skill in the art will appreciate that electrodes 20 may be distributed on substrate 2 in a variety of ways. As will be appreciated by those skilled in the art, the term "coplanar," as used herein to describe electrodes 20, should be understood as encompassing those electrodes which are substantially coplanar (as well as those which are fully coplanar). Thus, individual electrodes 20 can be slightly raised, recessed, and/or angled as compared other coplanar electrodes 20 on planar substrates 2 and still be considered coplanar.

Test device 100 additionally includes a second planar substrate 8, which is structurally similar to planar substrate 2, disposed above the first conductive layer 4 along the transverse direction T. Planar substrate 8 may be substantially planar with a substantially planar upper surface and substantially planar lower surface of the planar substrate 8—both of which extend in the lateral direction A and the longitudinal direction L (as shown in FIG. 2) and are separated by a thickness extending along the transverse direction T. Planar substrate 8 contains conductive vias 18 (otherwise known as filled vias or 'through holes') which extend between the upper and lower surfaces of planar substrate 8. Planar substrates 2 and 8 may be formed using a variety of methods and materials known to a person of ordinary skill in the art. For example, planar substrate 2 may be flexible or rigid and may be constructed using, for example, standard PCB, flex PCB, PET, PI, ceramic, glass, etc. For example, planar substrate 2 may be made out of an inert substrate such as a dielectric, pressure sensitive adhesive, laminate, etc. . . .

Test device 100 further includes one or more immediate layers 6 disposed in between conductive layer 4 and second planar substrate 8 (e.g., above and adjacent to planar conductive layer 4 and below and adjacent to second planar substrate 8 along transverse direction T). Similar to planar substrates 2 and 8, intermediate layers 6 may be substantially planar with a substantially planar upper surface and substantially planar lower surface of the intermediate layer 6—both of which extend in the lateral direction A and the longitudinal direction L (as shown in FIG. 2) and are separated by a thickness extending along the transverse direction T. The intermediate layer(s) 6 may be formed using a variety of methods and materials known to a person of ordinary skill in the art. For example, intermediate layers 6 may be made out of an inert substrate such as a dielectric, pressure sensitive adhesive, laminate, etc. . . . Alternatively, intermediate layers 6 can be integrated into one or both of planar substrate 8 and conductive layer 4 by forming intermediate layer(s) 6 directly on the upper surface of conductive layer 4 or the lower surface of substrate 8. One or more of intermediate layer(s) 6 can be an isolating layer(s) made from a dielectric or insulating material which isolates one or more, up to all, of electrodes 20 from one or more, up to all, of conductive vias 18. Alternatively, intermediate layers 6 can provide conductive pathways which allow one or more, up to all, electrodes 20 and conductive vias 18 to be electrically connected to one another.

In the embodiment depicted in in FIGS. 1-4, test device 100 contains an intermediate layer 6B which defines a fluid flow channel 14. The flow channel 14 allows fluid to flow from an inlet to the outlet of the flow channel 14.

Test device 100 may also contain intermediate layers 6A and 6C disposed on opposing planar sides of the intermediate layer 6B. Intermediate layers 6A and 6C may define one or more sensing areas 16. Individual sensing areas 16 allow fluid traveling through the fluid flow channel 14 to come into contact with individual coplanar electrodes 20 of conductive layer 4 and conductive vias 18 of the second substrate layer 18, respectively. For example, the sensing areas 16 depicted in FIGS. 1-4 are circular apertures (which can also be referred to as reaction wells) which extend through the respective intermediate layers 6A and 6C. Sensing areas 16 may also be fully or partially filled with a chemical/reagent 24 which may react with fluid in the fluid flow channel 14 and produce an analyte that can be detected by the conductive layer 10 (as described below). In certain embodiments, intermediate layer 6C can function as a masking layer by protecting conductive layer 4 from damage during the fabrication process and by defining sensing areas

16. Alternatively, individual sensing areas 16 may also be defined without the need for intermediate layers 6A and 6C by applying chemicals and/or reagents directly on one or both of coplanar electrodes 20 and conductive vias 18 on the first or the second planar substrate 2 and 8, respectively. It should also be appreciated that one or both of intermediate layers 6A and 6C may be combined with intermediate layer 6B to form a combined intermediate layer which defines both a fluid flow channel 14 and one or more sensor areas 16.

Test device 100 further includes planar conductive layer 10 disposed on or adjacent to the upper surface of planar substrate 8. Stated differently, conductive layer 10 is disposed above planar substrate 8 along the transverse direction T and is coplanar with the upper surface of planar substrate 8. While conductive layer 10 includes one or more individual coplanar electrodes 22, as shown in FIG. 4, conductive layer 10 is represented by the designated shaded area in FIG. 2. Coplanar electrodes 22 may be formed and partitioned using a variety of methods and materials known to a person of ordinary skill in the art—such as those identified above with respect to coplanar electrodes 20. One or more, up to all, of coplanar electrodes 22 are in electrical contact with at least one respective conductive via 18 in planar substrate 8—thus allowing reactions taking place in the sensing area 16 to be detected by a medical device electrically coupled to coplanar electrode(s) 22.

As best shown in FIG. 1, sensing areas 16 in intermediate layer 6A opposes (i.e., is opposite) those sensing areas 16 in intermediate layer 6C with the flow channel 14 of intermediate layer 6B disposed in between. In this opposed configuration, sensing areas 16 in intermediate layer 6A face those sensing areas 16 in intermediate layer 6C. Stated differently, sensing areas 16 in intermediate layer 6C is disposed below the sensing area 16 in intermediate layer 6A along a line extending from the first planar substrate 2 to the second planar substrate 8 with the flow channel located in between the respective sensing areas 16 of intermediate layers 6A and 6C.

As illustrated in, for example, FIGS. 1 and 2, intermediate layers 6, dielectric layer 8, and conductive layer 10 are arranged such than an uncovered portion 26 of the first conductive layer 4 is visible when viewing the testing device 100 from above conductive layer 10 along the transverse direction T. For example, uncovered portion 26 may be visible from above because (1) one or more, up to all, of the intermediate layers 6, dielectric layer 8, and conductive layer 10 may have an area in the lateral direction A and the longitudinal direction L that is smaller than the area of the conductive layer 4, and/or (2) one or more, up to all, of the intermediate layers 6, dielectric layer 8, and conductive layer 10 are offset in one or both of the lateral direction A and the longitudinal direction L as compared to the conductive layer 4. The uncovered portion 26 of conductive layer 4 is disposed within the area indicated and has an area (in the lateral direction A and the longitudinal direction L) that is smaller than the comparative area of the entire conductive layer 4. It should also be understood that while the conductive layer 4 has two distinct uncovered portions 26 in FIGS. 1 and 2 (located on opposite edges of the testing device 100), other embodiments of the concepts herein may include one, two, three or more uncovered portions 26 located on, for example, one or more, up to all, of the edges of conductive layer 4.

Continuing with FIGS. 1 and 2, because the uncovered portion 26 of conductive layer 4 and conductive layer 10 are both visible when viewing the testing device 100 from above conductive layer 10 along the transverse direction T, the electrodes 20 and 22 located thereon can be accessed from the top of the device. These "top side" electrical contacts can be easily accessed by an associated medical instrument.

In yet another alternative embodiment of test device 100, the conductive layer 10, second substrate layer 8, and intermediate layer 6C of test device 100 can be replaced by a lid layer that is devoid of electrodes, vias, or sensing areas. Thus exposed areas 26 of conductive layer 4 would be the only conductive layer visible from the above the test device 100. Alternatively, such a lid layer may be placed on top of conductive layer 10. This lid layer is similar to the second substrate layer 8' discussed below with respect to FIGS. 5-7.

FIGS. 5-7 depict a second embodiment a low-volume test device 100'. FIG. 5 depicts a side view of a second embodiment of the low-volume sensing device. FIG. 6 depicts a top view of the second embodiment of the low-volume sensing device. FIG. 7 depicts an exploded side view of the second embodiment of the low-volume sensing device. In the following description of test devices 100', it should be noted that similar reference numbers to those used to describe test device 100 in FIGS. 1-4 are intended to refer to similar features (unless stated otherwise)—thus avoiding the need to duplicate the detailed description of those features.

As best shown in FIG. 5, test device 100' has a first planar substrate 2', a first conductive layer 4', and an intermediate layers 6A', 6B', and 6C'. Test device 100' further comprises a second conductive layer 10' disposed on or adjacent to the upper surface of intermediate layer 6C' along the transverse direction T, as opposed to the position of conductive layer 10 in FIGS. 1-4. As with conductive layer 10, while conductive layer 10' includes one or more individual coplanar electrodes 22', conductive layer 10' is generally represented by the designated shaded area in FIG. 6. One or more, up to all, of coplanar electrodes 22' are in electrical contact with at least one respective sensing area 16' in intermediate layer 6C'—thus allowing reactions taking place in the sensing area 16' to be detected by a medical device electrically coupled to coplanar electrode(s) 22'.

Test device 100' further includes a substrate layer 8' disposed on or adjacent to the upper surface of the second conductive layer 10' along the transverse direction T. Planar substrates 2' and 8' may be formed using a variety of methods and materials known to a person of ordinary skill in the art. For example, planar substrate 2' or 8' may be flexible or rigid and may be constructed using, for example, standard PCB, flex PCB, PET, PI, ceramic, glass, etc. For example, planar substrate 2' or 8' may be made out of an inert substrate such as a dielectric, pressure sensitive adhesive, laminate, etc. . . . In one embodiment, substrate 8' may be a simple laminate layer which acts as a cover, thereby protecting the individual electrodes 22' from accidental damage.

As illustrated in, for example, FIGS. 5 and 6, second planar substrate 8' in test device 100' is configured such than an uncovered portion 28 of the second conductive layer 10' is visible when viewing the testing device 100' from above second conductive layer 4' along the transverse direction T. For example, uncovered portion 28 may be visible from above because (1) second planar substrate 8' has an planar area in the lateral direction A and the longitudinal direction L that is smaller than the planar area of the conductive layer 10, and/or (2) second planar substrate 8' is offset in one or both of the lateral direction A and the longitudinal direction L as compared to the conductive layer 10'. The uncovered portion 28 of second conductive layer 10' is disposed within the area indicated and has an area (in the lateral direction A and the longitudinal direction L) that is smaller than the comparative area of the entire conductive layer 4. It should also be understood that while the second conductive layer 10' has two distinct uncovered portions 28 in FIGS. 5 and 6 (located on opposite edges of the testing device 100'), other embodiments of the concepts herein may include one, two, three or more uncovered portions 28 located, for example, one or more, up to all, of the edges of conductive layer 10'.

A person of ordinary skill in the art should also appreciate that there are a variety of methods which may be used to manufacture the test device 100 and 100', as described above. Furthermore, person of ordinary skill in the art should further appreciate that a variety of medical instruments can be adapted to interface with testing devices with top side contacts, such as testing devices 100 and 100'.

What is claimed is:

1. A test device comprising:
    a first planar intermediate isolating layer with at least a first sensing area;
    a second planar intermediate isolating layer with at least a second sensing area;
    a third planar intermediate isolating layer with a flow channel 14, wherein the first sensing area opposes the second sensing area with the flow channel disposed in between the first sensing area and the second sensing area;
    a first planar conductive layer disposed adjacent to the first intermediate isolating layer opposite the third planar intermediate isolating layer;
    a first planar substrate disposed adjacent to the first planar conductive layer opposite the first intermediate isolating layer;
    a second planar substrate disposed adjacent to the second planar intermediate isolating layer opposite the third planar intermediate isolating layer, the second planar substrate having at least a first conductive via in electrical contact with the second sensing area; and
    a second planar conductive layer disposed adjacent to the second planar substrate opposite the second planar intermediate isolating layer, the second planar conductive layer being in electrical contact with first conductive via,
    wherein each of the first planar intermediate isolating layer, the second planar intermediate isolating layer, the third planar intermediate isolating layer, first planar conductive layer, the first planar substrate, the second planar substrate, and the second planar conductive layer have two planar surfaces separated by a thickness, each of the respective two planar surface having an planar area that is approximately equal,
    wherein the planar area of first conductive layer is greater than the planar area of each of the first planar intermediate isolating layer, the second planar intermediate isolating layer, the third planar intermediate isolating layer, the second planar substrate, and the second planar conductive layer.

2. The test device of claim 1, wherein an uncovered portion of the first planar conductive layer is uncovered by each of the first planar intermediate isolating layer, the second planar intermediate isolating layer, the third planar intermediate isolating layer, the second planar substrate, and the second planar conductive layer when viewed from above the test device; and
    wherein a coplanar electrode is at least partially disposed on the uncovered portion of the first planar conductive layer.

3. The test device of claim 1, wherein each of the first planar intermediate isolating layer, the second planar intermediate isolating layer, the third planar intermediate isolating layer, the second planar substrate, and the second planar conductive layer have an equal planar area.

4. A test device comprising:
    a first planar intermediate isolating layer with at least a first sensing area;
    a second planar intermediate isolating layer with at least a second sensing area;
    a third planar intermediate isolating layer with a flow channel 14, wherein the first sensing area opposes the second sensing area with the flow channel disposed in between the first sensing area and the second sensing area;
    a first planar conductive layer disposed adjacent to the first intermediate isolating layer opposite the third planar intermediate isolating layer;
    a first planar substrate disposed adjacent to the first planar conductive layer opposite the first intermediate isolating layer;
    a second planar conductive layer disposed adjacent to the second planar intermediate isolating layer opposite the third planar intermediate isolating layer; and
    a second planar substrate disposed adjacent to the second planar conductive layer opposite the second planar intermediate isolating layer,
    wherein each of the first planar intermediate isolating layer, the second planar intermediate isolating layer, the third planar intermediate isolating layer, first planar conductive layer, the first planar substrate, the second planar substrate, and the second planar conductive layer have two planar surfaces separated by a thickness, each of the respective two planar surface having an planar area that is approximately equal,
    wherein the planar area of first conductive layer is greater than the planar area of each of the first planar intermediate isolating layer, the second planar intermediate isolating layer, the third planar intermediate isolating layer, the second planar substrate, and the second planar conductive layer,
    wherein the planar area of the second planar conductive layer is greater than the planar area of the second planar substrate.

5. The test device of claim 4, wherein an uncovered portion of the first planar conductive layer is uncovered by each of the first planar intermediate isolating layer, the second planar intermediate isolating layer, the third planar intermediate isolating layer, the second planar substrate, and the second planar conductive layer when viewed from above the test device,
    wherein an uncovered portion of the second planar conductive layer is uncovered by than the planar area of the second planar substrate, and
    wherein a first coplanar electrode is at least partially disposed on the uncovered portion of the first planar conductive layer and a second coplanar electrode is at least partially disposed on the uncovered portion of the second planar conductive layer.

6. The test device of claim 1, wherein each of the first planar intermediate isolating layer, the second planar intermediate isolating layer, the third planar intermediate isolating layer, and the second planar conductive layer have an equal planar area, and
    wherein second planar substrate has a planar area that is less than the first planar intermediate isolating layer, the second planar intermediate isolating layer, the third planar intermediate isolating layer, and the second planar conductive layer.

7. A system comprising:
the test device of claim 1; and
a medical device configured to interface with the test device.

* * * * *